(12) United States Patent
Enomoto et al.

(10) Patent No.: US 9,878,583 B2
(45) Date of Patent: Jan. 30, 2018

(54) VEHICLE ALERTNESS CONTROL SYSTEM

(71) Applicant: TOYOTA JIDOSHA KABUSHIKI KAISHA, Toyota-shi, Aichi-ken (JP)

(72) Inventors: Takaaki Enomoto, Anjo (JP); Satoshi Nakagawa, Okazaki (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 15/149,874

(22) Filed: May 9, 2016

(65) Prior Publication Data

US 2017/0080856 A1 Mar. 23, 2017

(30) Foreign Application Priority Data

Sep. 17, 2015 (JP) ................................ 2015-184245

(51) Int. Cl.
  *G08B 23/00* (2006.01)
  *B60C 9/00* (2006.01)
  *A61B 5/18* (2006.01)

(52) U.S. Cl.
  CPC . *B60C 9/00* (2013.01); *A61B 5/18* (2013.01)

(58) Field of Classification Search
  CPC ............ G08B 21/06; A61B 5/18; B60Q 9/008
  USPC ............................ 340/576, 575, 425.5; 701/1
  See application file for complete search history.

(56) References Cited

U.S. PATENT DOCUMENTS

| | | | | |
|---|---|---|---|---|
| 6,147,612 A | * | 11/2000 | Ruan | G08B 21/06 340/573.1 |
| 7,652,583 B2 | * | 1/2010 | Sanchez | B60K 28/066 340/575 |
| 2003/0181822 A1 | * | 9/2003 | Victor | A61B 3/113 600/558 |
| 2008/0238694 A1 | * | 10/2008 | Ishida | A61B 5/18 340/575 |
| 2011/0021866 A1 | * | 1/2011 | Iizuka | A61B 3/113 600/26 |
| 2012/0212353 A1 | * | 8/2012 | Fung | B60K 28/06 340/905 |

FOREIGN PATENT DOCUMENTS

| | | |
|---|---|---|
| JP | 2010-134534 A | 6/2010 |
| JP | 2013-171546 A | 9/2013 |

* cited by examiner

*Primary Examiner* — Phung Nguyen
(74) *Attorney, Agent, or Firm* — Sughrue Mion, PLLC

(57) ABSTRACT

A vehicle alertness control system that executes alertness control to increase an alertness level of a driver of a vehicle includes an alertness level determination unit, an alertness controller, and a conversation controller. The alertness level determination unit is configured to determine an alertness level of the driver. The alertness controller is configured to select a level of a stimulus applied to the driver based on the determined alertness level. The conversation controller is configured to select a conversation category corresponding to the selected stimulus level from conversation categories categorizing a content of utterance in correspondence with each stimulus level and control conversation with the driver through a speaker and a microphone.

8 Claims, 9 Drawing Sheets

Fig.4

| stimulus level | stimulus strength learned value P1 | conversation period P2 | seat vibration strength P3 | seat vibration cycle P4 | air conditioner blow amount P5 |
|---|---|---|---|---|---|
| low | 0 | T1 | | | |
| | 1 | T1+α | | | |
| | 2 | T1+2α | | | |
| | ... | ... | | | |
| | N (upper limit value) | T1+Nα | | | |
| medium | 0 | T2 | A2 | S2 | |
| | 1 | T2+α | A2+β | S2-γ | |
| | 2 | T2+2α | A2+2β | S2-2γ | |
| | ... | ... | ... | ... | |
| | N (upper limit value) | T2+Nα | A2+Nβ | S2-Nγ | |
| high | 0 | T3 | A3 | S3 | B3 |
| | 1 | T3+α | A3+β | S3-γ | B3+δ |
| | 2 | T3+2α | A3+2β | S3-2γ | B3+2δ |
| | ... | ... | ... | ... | ... |
| | N (upper limit value) | T3+Nα | A3+Nβ | S3-Nγ | B3+Nδ |

| stimulus level | conversation category | conversation examples | Concepts |
|---|---|---|---|
| low | A | vehicle:Hello, ___.<br>Today is a fine day.<br>driver:Yes. | drawing a reflex response |
| medium | B | vehicle:The football World Cup has begun.<br>vehicle:Do you know yesterday's result of Japan's game?<br>driver:No, I don't.<br>vehicle:Japan won _ to _.<br>vehicle:Which country do you support?<br>driver:___.<br>vehicle:It would be nice if ___ and Japan can go to the World Cup. | short conversation<br><br>conversation is formed based on personal hobby preference (sport)<br><br>drawing a simple response |
| high | C | vehicle:You can see Mt.Fuji to the north.<br>You can see it well because it's a fine day.<br>driver:It's beautiful.<br>vehicle:Would you like to drive on a different route?<br>driver:Why?<br>vehicle:It's nice to see Mt.Fuji from a different direction.<br>vehicle:There are three recommended routes.<br>(recommend based on personal preference (food, shopping))<br>The first route is ···.<br>The second route is ···.<br>The third route is ···.<br>driver:I'll choose the first route.<br>vehicle:Okay. | long conversation<br><br>(continuing conversation by combining travelling scene with personal preference, etc.)<br><br>inducing driver to think and act |

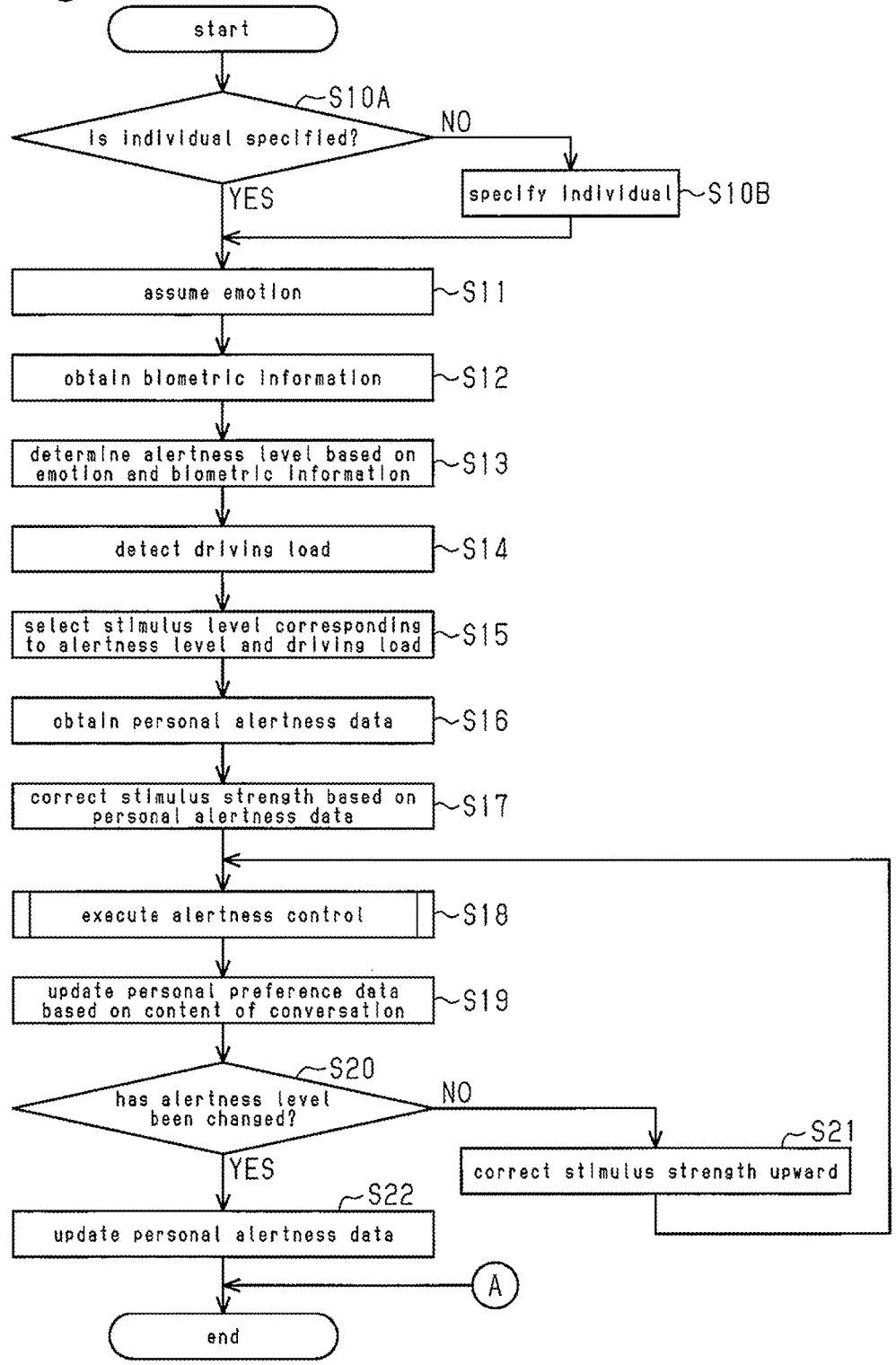

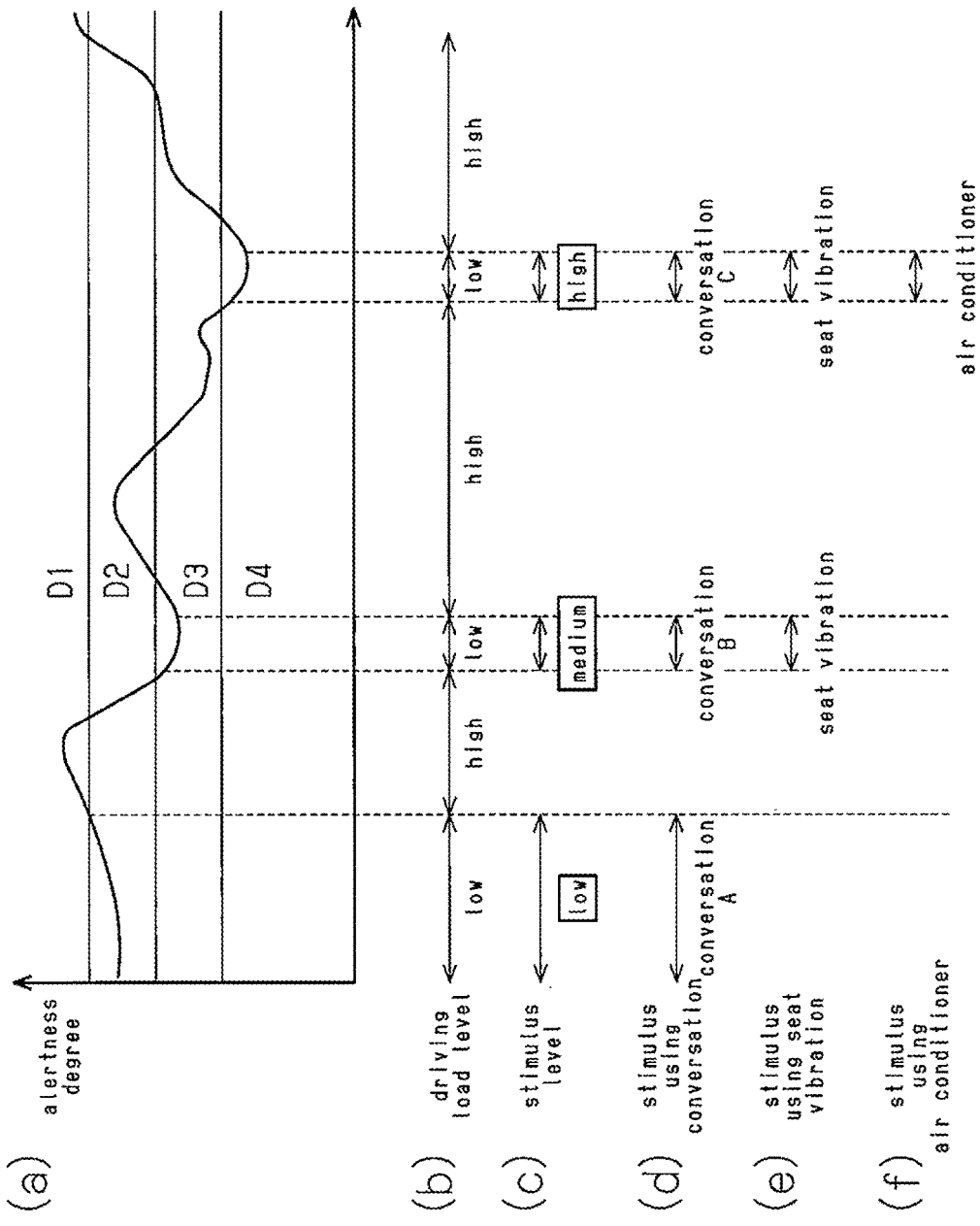

VEHICLE ALERTNESS CONTROL SYSTEM

BACKGROUND OF THE INVENTION

The present disclosure relates to a vehicle alertness control system that alerts a vehicle driver when the alertness of the driver decreases, that is, when the driver becomes drowsy.

Japanese Laid-Open Patent Publication No. 2013-171546 describes one example of a vehicle alertness control system. The system is configured to accumulate log data in an alertness list by associating the present alertness of the driver with the vehicle driving state and the music reproduction mode. The vehicle drive state is obtained from the vehicle speed, the acceleration, and the like. The music reproduction mode is defined by the genre, tempo, volume, and the like of the music reproduced in the passenger compartment. When the alertness of the driver becomes less than a predetermined value, the system refers to the alertness list to select the music reproduction mode that is likely to increase the alertness of the driver. That is, the system selects the music reproduction mode that was used when the driver alertness was high. Then, the system replays music in the selected reproduction mode to alert the driver.

In the system described in Japanese Laid-Open Patent Publication No. 2013-171546, the personal preference of the driver is considered to alert the driver. However, the process that increases the alertness is performed on the driver in a unidirectional manner. Thus, there is still room for improvement to further accurately increase the alertness of the driver.

SUMMARY OF THE INVENTION

It is an object of the present disclosure to provide a vehicle alertness control system that executes sophisticated alertness control by involving the driver as a partner when increasing the alertness of the driver.

One aspect of the present disclosure is a vehicle alertness control system configured to execute alertness control that increases an alertness level of a driver of a vehicle. The vehicle alertness control system includes an alertness level determination unit, an alertness controller, and a conversation controller. The alertness level determination unit is configured to determine an alertness level, which is a hierarchized alertness degree of the driver, based on at least one of an assumption result obtained from an emotion assumption unit that is configured to monitor behavior of the driver and assume an emotion of the driver and a detection result obtained from a biometric sensor that detects a biosignal of the driver. The alertness controller is configured to select a level of a stimulus applied to the driver based on the determined alertness level. The conversation controller is configured to select a conversation category corresponding to the selected stimulus level and control conversation with the driver through a speaker and a microphone. The conversation category is selected from conversation categories categorizing a content of utterance in correspondence with each stimulus level.

Another aspect of the present disclosure is a vehicle alertness control system configured to execute alertness control that increases an alertness level of a driver of a vehicle and including a control circuitry. The control circuitry is configured to execute at least one of monitoring behavior of the driver to assume an emotion of the driver and receiving a detection result from a biometric sensor that detects a biosignal of the driver. The control circuitry is configured to determine an alertness level, which is a hierarchized alertness degree of the driver, based on at least one of the driver emotion assumption result and the detection result of the biometric sensor. The control circuitry is configured to select a level of a stimulus applied to the driver based on the determined alertness level. The control circuitry is configured to select a conversation category that corresponds to the selected stimulus level from conversation categories that categorize a content of utterance corresponding to each stimulus level and control conversation with the driver through a speaker and a microphone.

Another aspect of the present disclosure is a method executed by a control system. The method includes at least one of monitoring behavior of a driver of a vehicle to assume an emotion of the driver and receiving a detection result from a biometric sensor that detects a biosignal of the driver. The method includes determining an alertness level, which is a hierarchized alertness degree of the driver, based on at least one of the driver emotion assumption result and the detection result of the biometric sensor. The method includes selecting a level of a stimulus applied to the driver based on the determined alertness level. The method includes selecting a conversation category corresponding to the selected stimulus level from conversation categories that categorize a content of utterance in correspondence with each stimulus level and controlling conversation with the driver through a speaker and a microphone.

Other aspects and advantages of the invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which:

FIG. 4 is a schematic diagram showing one example of contents set in a stimulus strength correction table that is used by the vehicle alertness control system shown in FIG. 1;

FIG. 6 is a schematic diagram showing one example of contents of conversations in categories corresponding to stimulus levels;

FIG. 7 is a flowchart showing the procedures of alertness control executed by the vehicle alertness control system shown in FIG. 1;

FIG. 9 is a time chart showing an example of changes in elements when the vehicle alertness control system shown in FIG. 1 executes the alertness control.

DESCRIPTION OF THE PREFERRED EMBODIMENTS

The present embodiment of a vehicle alertness control system monitors the behavior and biosignals of the driver when the vehicle is traveling. When determined that the alertness level of the driver is decreased, the vehicle alertness control system executes alertness control that involves the driver in conversation to increase the alertness level. Normally, as the driver alertness level is decreased, the level of a stimulus needed to increase the alertness level becomes higher. Thus, the conversational alertness control changes conversation categories to increase the stimulus level as the driver alertness level is decreased. When the driver is in a situation in which a driving load is high, for example, when traveling on a curve, the driver needs to concentrate on the driving operation. Thus, under such a situation, the conversation for controlling alertness would adversely increase a burden of the driver. In this regard, the present embodiment also monitors the driving load on the driver when the vehicle is traveling and prohibits execution of the conversational alertness control when determined that the driving load is high.

Figure 1:
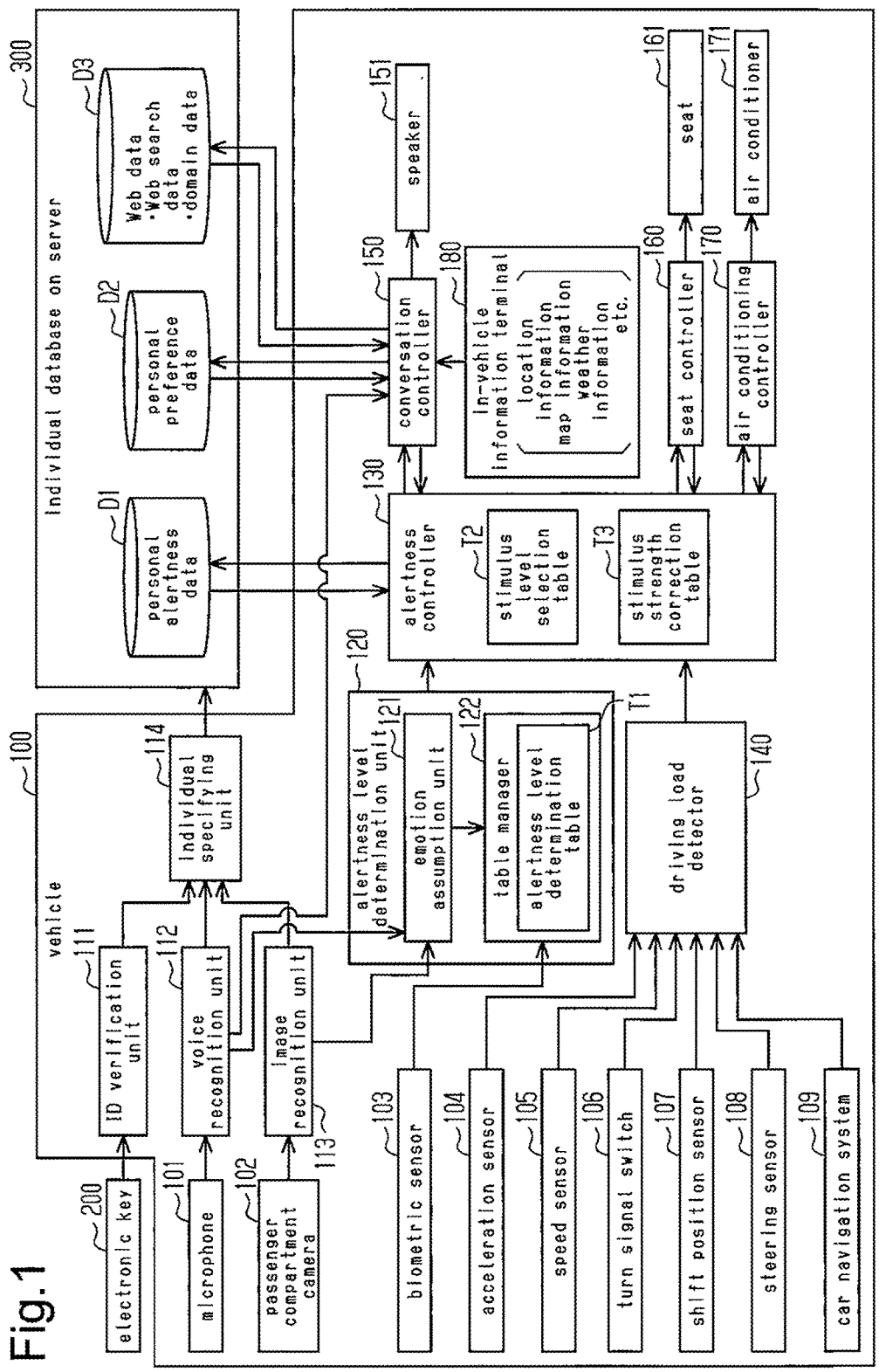
FIG. 1 is a schematic block diagram showing the configuration of one embodiment of a vehicle alertness control system.

The structure of the system of the present embodiment will now be described with reference to the drawings. As shown in FIG. 1, a vehicle 100 includes an ID verification unit 111, which verifies an ID (identification code) of an electronic key 200 carried by the driver through wireless communication with the electronic key 200. The ID verification unit 111 sends the verified ID of the electronic key 200 to an individual specifying unit 114.

The vehicle 100 also includes a voice recognition unit 112, which performs a voice recognition process on a voice signal that is received from the driver through a microphone 101. The voice recognition unit 112 performs a frequency analysis on the received voice signal to extract the voiceprint of the driver. The voice recognition unit 112 sends the extracted voiceprint to the individual specifying unit 114. In the present embodiment, in addition to the voiceprint extraction, the voice recognition unit 112 extracts a voice expression feature amount related to voice prosody, which is used to evaluate the voice expression, and converts the voice into text.

The vehicle 100 also includes an image recognition unit 113, which performs an image recognition process on a captured image of the driver received from a passenger compartment camera 102. The image recognition unit 113 calculates a feature amount of a face, including eyes, a nose, and a mouth, for example, from the captured image of the driver. The image recognition unit 113 sends the extracted face feature amount to the individual specifying unit 114. In the present embodiment, in addition to the extraction of the face feature amount, the image recognition unit 113 extracts information related to movement of the driver sight line, which is used when evaluating the face expression, and a feature amount of actions including a gesture and vehicle operation of the driver.

When receiving the identification information of the electronic key 200, the voiceprint of the driver, and the face feature amount of the driver, the individual specifying unit 114 uses the combination of the pieces of information to specify the driver. In one example of such a specification process, persons that have used the electronic key 200 are extracted as driver candidates, for example, based on the identification information of the electronic key 200, and the driver is selected from the candidates based on the voiceprint and the face feature amount of the driver. The individual information of the specified driver is transmitted from the individual specifying unit 114 to an individual database 300 located on an external server and used when accessing data maintained for each individual driver in the individual database 300. In the description hereafter, it is assumed that the vehicle 100 and the individual database 300, which is located on the server, exchange signals and data through a wireless communication device (not shown).

The data maintained in the individual database 300 includes personal alertness data D1, which optimizes the alertness control taking into consideration personal differences among drivers in response to a stimulus. The data maintained in the individual database 300 also includes personal preference data D2, which indicates the personal preference such as favorite sports or hobbies of a driver, and Web data D3, which is obtained through an internet connection and, for example, the history of information searches performed by the driver or domain information of homepages posting various genres of topical information such as news and entertainment.

An alertness level determination unit 120 receives a sequence of behavior including voice expression, which includes the voice expression feature amount extracted by the voice recognition unit 112 and sight line movement, a gesture, or vehicle operation of the driver extracted by the image recognition unit 113. The alertness level determination unit 120 includes an emotion assumption unit 121, which is used to assume the emotions of the driver.

When the emotion assumption unit 121 assumes the emotions of the driver, determination references are set to distinguish predetermined emotions, for example, "excited," "happy," "relaxed," "bored," "sad," "irritated," and "nervous," through a statistical process performed on training data that is categorized for each emotion. When the emotion assumption unit 121 receives the voice expression feature amount, the face expression feature amount, and the action feature amount as unknown data, the emotions of the driver are assumed based on the determination references, which has been set. The alertness level determination unit 120 uses the assumed emotions of the driver to determine an alertness level of the driver. The alertness level is a hierarchized alertness degree. In the present embodiment, the alertness level is hierarchized into four ranks, namely, "D1," "D2," D3," and "D4," in order from ones having a higher alertness degree.

Figure 2:
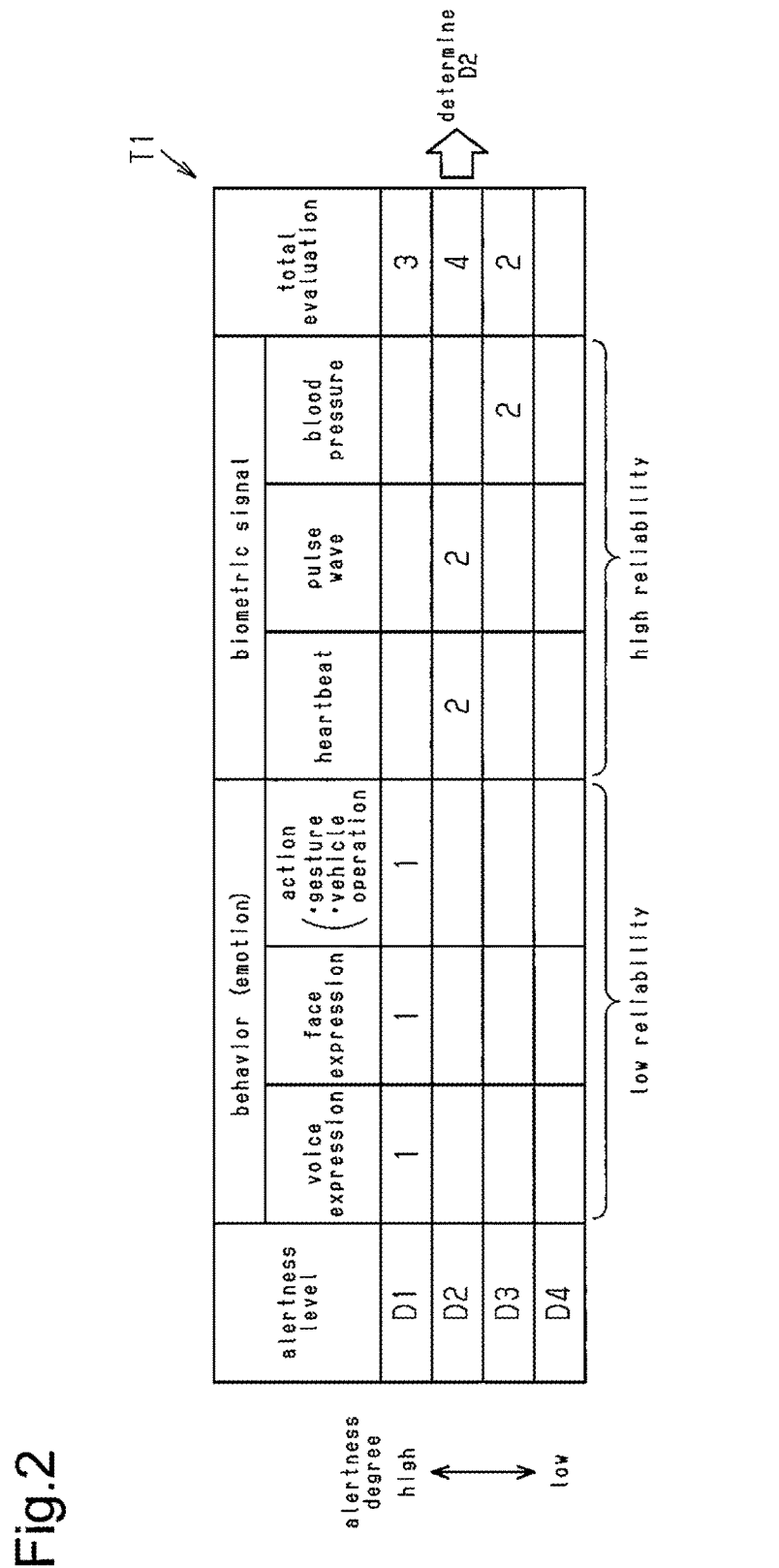
FIG. 2 is a schematic diagram showing one example of contents set in an alertness level determination table that is used by the vehicle alertness control system shown in FIG. 1.

The alertness level determination unit 120 determines the driver alertness level using a table manager 122, which includes an alertness level determination table T1 shown in FIG. 2, in addition to a detection result of a biometric sensor 103, which detects a biosignal such as a heartbeat, a pulse wave, or blood pressure of the driver.

FIG. 2 shows an example of the alertness level determination table T1 in which the determination result of the driver alertness level based on the voice expression of the driver, the determination result of the driver alertness level based on the face expression of the driver, and the determination result of the driver alertness level based on the actions (gesture, vehicle operation) of the driver are each "D1." The determination result of the driver alertness level based on the heartbeat of the driver and the determination result of the driver alertness level based on the pulse wave of the driver are each "D2." The determination result of the driver alertness level based on the blood pressure of the driver is "D3."

When the driver alertness level is determined based on different kinds of data, the determination results may vary. In this regard, in the present embodiment, the determination result of the alertness levels "D1" to "D4" based on each kind of data is quantified, and the obtained numeral values are added for each alertness level. The alertness level having the largest added value is determined to be the driver alertness level. When quantifying the alertness level determination results of each kind of data, the determination result based on the biometric information (heartbeat, pulse wave, blood pressure) of the driver is weighted more than (in FIG. 2, twice as much as) the determination result based on the emotions (voice expression, face expression, actions) of the driver. This is because the determination result of the driver alertness level based on the biometric information of the driver is considered more reliable than that based on the behavior of the driver. Thus, in the example shown in FIG. 2, "D2" has the largest added value of "4," which is the determination results of the driver alertness level based on the heartbeat and pulse wave of the driver. The alertness level "D2" is determined to be the driver alertness level. When different alertness levels have the same added value of the determination result, for example, the lowest alertness level may be determined to be the driver alertness level.

As shown in FIG. 1, the driver alertness level, which is determined by the alertness level determination unit 120, is sent from the alertness level determination unit 120 to an alertness controller 130. When executing the alertness control on the driver, the alertness controller 130 selects a stimulus level that is applied to the driver using the driver alertness level obtained from the alertness level determination unit 120 and referring to a stimulus level selection table T2 shown in FIG. 3. In the present embodiment, conversational control, seat vibration control, and control that adjusts the blow amount of the air conditioner, are executed as the alertness control performed on the driver in accordance with the selected stimulus level.

Figure 3:
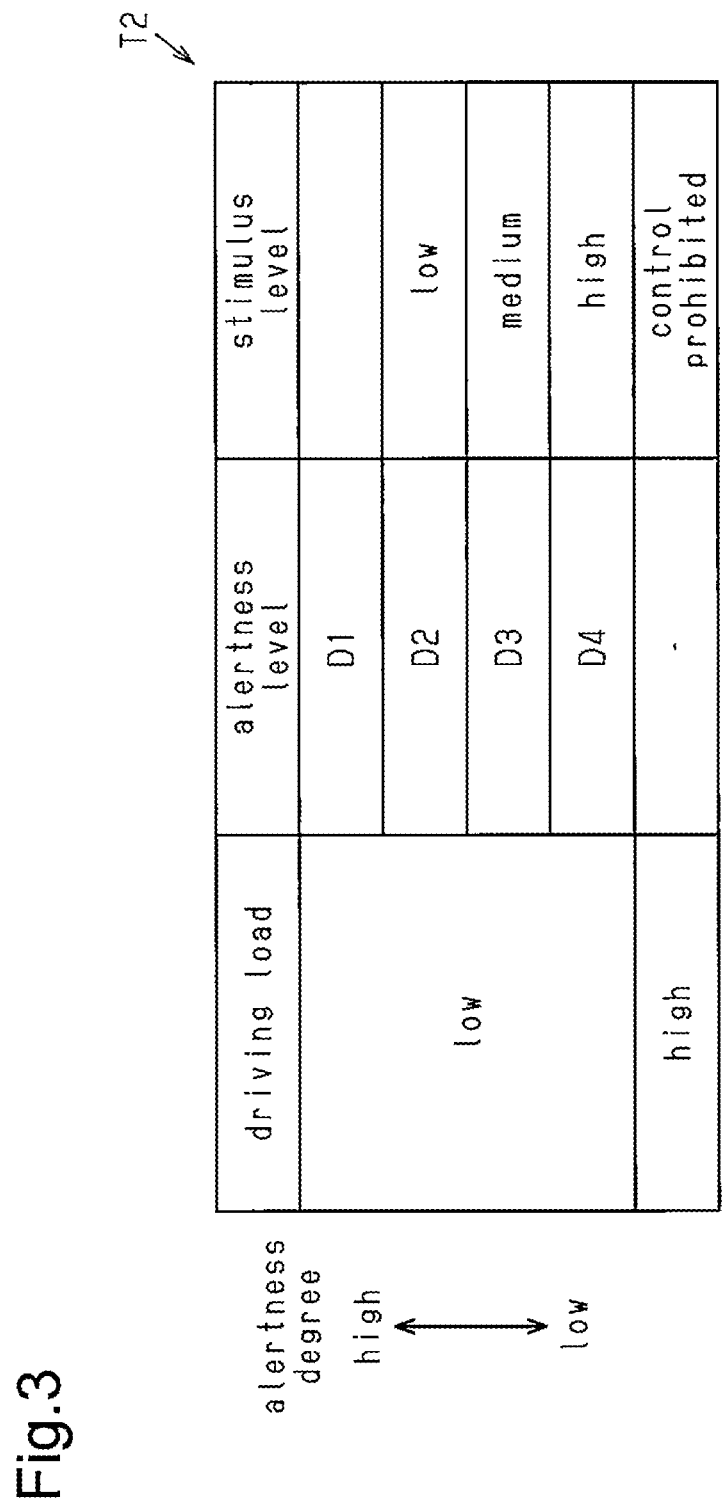
FIG. 3 is a schematic diagram showing one example of contents set in a stimulus level selection table that is used by the vehicle alertness control system shown in FIG. 1.

FIG. 3 shows an example of the stimulus level selection table T2 in which stimulus levels applied to the driver are set in accordance with the driver alertness levels in association with classifications ("low," "high") whether or not the driving load on the driver is greater than or equal to a predetermined value. More specifically, when the driving load on the driver is less than the predetermined value, or classified as "driving load: low," "low," "medium," and "high" are set as the stimulus levels corresponding to the driver alertness levels "D2," "D3," and "D4." In the stimulus level selection table T2, the stimulus level corresponding to the driver alertness level "D1" has no content. Thus, in the present embodiment, when the driver alertness level is "D1," the alertness control including the conversational control is not performed on the driver. When the driving load on the driver is greater than or equal to the predetermined value, or classified as "driving load: high," "control prohibited" is set as the corresponding stimulus level to prohibit the alertness control including the conversational control from being performed on the driver regardless of the driver alertness level being any one of "D1" to "D4." This is because when the driver is under a high driving load situation, the driver needs to concentrate on the driving operation. In such a situation, the alertness control would adversely increase a burden of the driver.

As shown in FIG. 1, the driving load on the driver is detected by a driving load detector 140. When a steep acceleration or deceleration is determined based on, for example, a detection value of an acceleration sensor 104 or a speed sensor 105, the driving load on the driver is detected to be high. Additionally, when determined that the various operations are frequently performed on the vehicle 100 based on, for example, a detection value of a turn signal switch 106, a shift position sensor 107, or a steering sensor 108, the driving load on the driver is also detected to be high. Additionally, when determined that the vehicle 100 is located in an environment that is difficult to drive in, for example, a road with a few lanes, a narrow road, or a road having a large curvature, based on information obtained from a car navigation system 109, the driving load on the driver is also detected to be high.

When performing the alertness control on the driver, the alertness controller 130 corrects the stimulus strength of the stimulus level applied to the driver using the personal alertness data D1, which is stored in the individual database 300, and referring to a stimulus strength correction table T3 shown in FIG. 4. The personal alertness data D1 initially sets a learned value P1 of the stimulus strength that is used when performing the alertness control on the driver. The learned value P1 tends to be increased as a driver has a lower sensitivity to the alertness stimulus.

FIG. 4 shows an example of the stimulus strength correction table T3 in which the stimulus strengths are separately set in correspondence with the learned values P1 of the stimulus strength, which are initially set based on the personal alertness data D1. More specifically, in the stimulus strength correction table T3, "T1," "T2," and "T3" that are values of a conversation period P2 corresponding to the stimulus strength learned value P1 of "0" are set in correspondence with the stimulus levels "low," "medium," and "high," respectively. In this case, the conversation period P2 corresponding to the stimulus levels satisfies the relationship of "T1"<"T2"<"T3." The conversation period P2 is set to be increased by a fixed value "a" whenever the stimulus strength learned value P1 is incremented by "1." When performing the seat vibration alertness control on the driver, "A2" and "A3" that are values of a seat vibration strength P3 corresponding to the stimulus strength learned value P1 of "0" are set in correspondence with the stimulus levels "medium" and "high," respectively. In this case, the seat vibration strength P3 corresponding to the stimulus levels satisfies the relationship of "A2"<"A3." The seat vibration strength P3 is set to be increased by a fixed value "β" whenever the stimulus strength learned value P1 is incremented by "1." Additionally, when performing the seat vibration alertness control on the driver, "S2" and "S3" that are values of a seat vibration cycle P4 corresponding to the stimulus strength learned value P1 of "0" are set in correspondence with the stimulus levels "medium" and "high," respectively. In this case, the seat vibration cycle P4 corresponding to the stimulus levels satisfies the relationship of "S2">"S3." The seat vibration cycle P4 is set to be decreased by a fixed value "γ" whenever the stimulus strength learned value P1 is incremented by "1." When performing the air conditioner alertness control on the driver, "B3" that is a value of a blow amount P5 of the air conditioner corresponding to the stimulus strength learned value P1 of "0" is set in correspondence with the stimulus level "high." The air conditioner blow amount is set to be increased by a fixed value "δ" whenever the stimulus strength learned value P1 is incremented by "1." In the example of the stimulus strength correction table T3 shown in FIG. 4, when the stimulus strength learned value P1 is incremented, the conversation period P2, the seat vibration strength P3, the seat vibration cycle P4, and the air conditioner blow amount P5 are changed corresponding to each stimulus level. Instead of or in addition, for example, the volume of the conversation, the temperature of a seat 161, or the temperature of the air conditioner may be changed.

As shown in FIG. 1, the alertness controller 130 sends information of the stimulus level, which is selected referring to the stimulus level selection table T2 shown in FIG. 3, and information of the stimulus strength, which is corrected referring to the stimulus strength correction table T3 shown in FIG. 4, to a conversation controller 150. The conversational alertness control is executed by the conversation controller 150.

Figure 5:
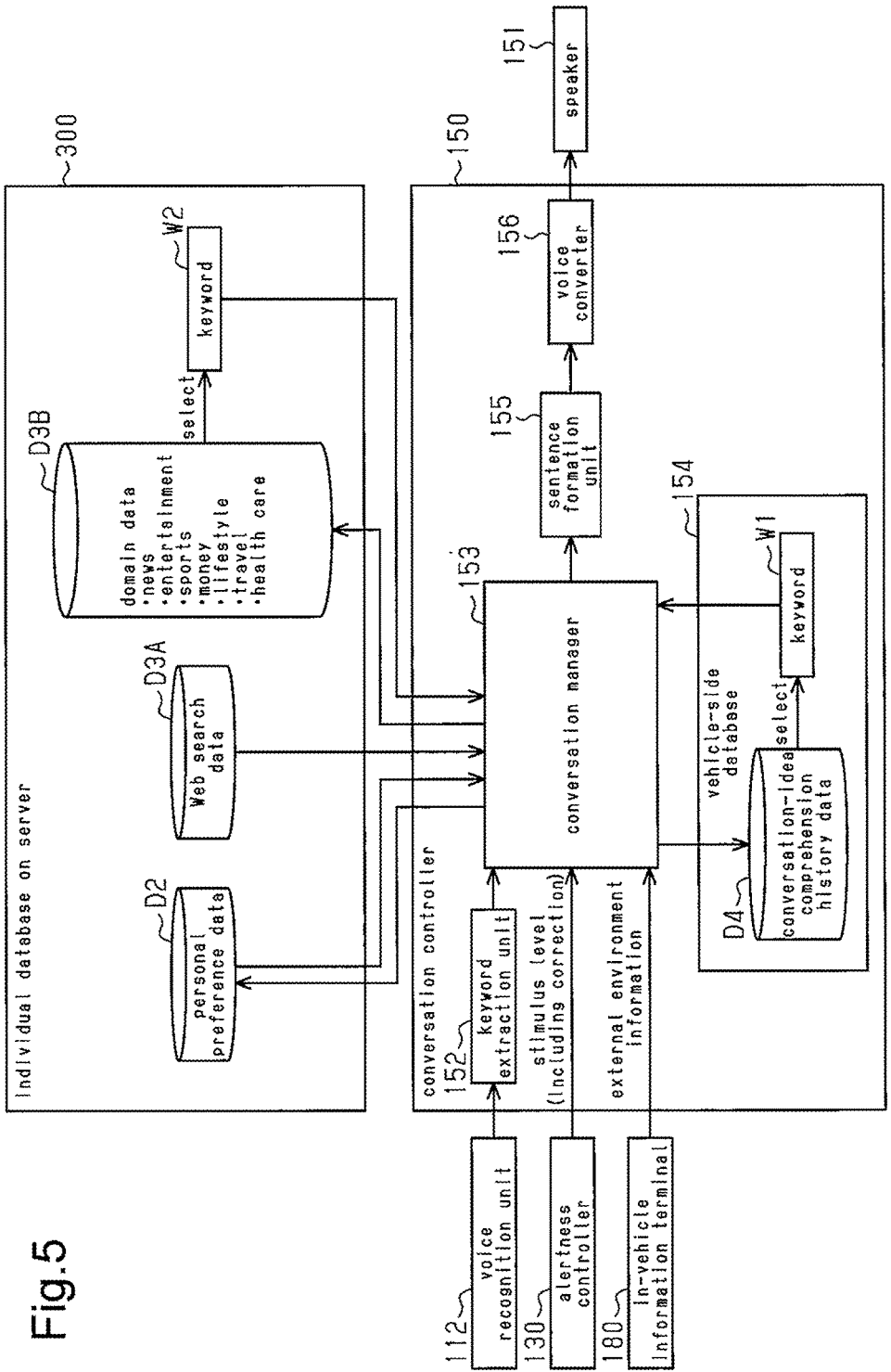
FIG. 5 is a block diagram showing an example of the internal configuration of the conversation controller shown in FIG. 1.

More specifically, as shown in FIG. 5, when text data that indicates a content uttered by the driver is sent from the voice recognition unit 112 to a keyword extraction unit 152, the keyword extraction unit 152 analyzes the text data to detect the beginning and the end of the utterance of the driver. The keyword extraction unit 152 extracts keywords from the text data contained in the beginning to the end of the utterance. The keyword extraction unit 152 sends the extracted keywords to a conversation manager 153. The conversation manager 153 assumes an idea of the driver based on the frequency of the keywords or the like. The conversation manager 153 accumulates the history of the assumed driver idea in a vehicle-side database 154 as conversation-idea comprehension history data D4. Based on the accumulated conversation-idea comprehension history data D4, a keyword W1 that is used in conversation with the driver is selected from groups of keywords, which are prepared in the vehicle-side database 154 in advance.

If the stimulus level received from the alertness controller 130 is "medium" or "high" when executing the conversational alertness control, the conversation manager 153 also accesses the individual database 300 located on the server and obtains the personal preference data D2, which indicates the personal preference such as favorite sports or hobbies of the driver. The conversation manager 153 also obtains Web search data D3A, which indicates the history of information searches performed by the driver, in addition to the personal preference data D2. Based on the personal preference data D2 and the Web search data D3A, the conversation manager 153 selects a genre that conforms to the preference of the driver from domain data D3B stored in the individual database 300. Based on the frequency of keywords appeared in the homepage specified by the domain of the selected genre or the like, the conversation manager 153 selects a keyword W2 that is used in conversation with the driver. This increases the frequency of the topic about the preference of the driver appeared in the conversation with the driver. Here, the term of "conversation" refers to a sequence of a story that is completed through one or more interchanges with the driver. FIG. 6 is a table showing examples of such conversation that are determined for each stimulus level. The Web search data D3A and the domain data D3B correspond to the Web data D3 shown in FIG. 1.

If the stimulus level received from the alertness controller 130 is "high" when executing the conversational alertness control, the conversation manager 153 also accesses an in-vehicle information terminal 180 and obtains vehicle external environment information, for example, location information of the vehicle 100, map information, or weather information. Based on the vehicle external environment information received from the in-vehicle information terminal 180, the conversation manager 153 obtains a keyword that is used in conversation with the driver. This increases the frequency of the topic about the external environment information of the vehicle 100 appeared in the conversation with the driver.

The conversation controller 150 sends the keywords, which are obtained by the conversation manager 153 from the vehicle-side database 154, the individual database 300, and the in-vehicle information terminal 180, to a sentence formation unit 155. The sentence formation unit 155 combines the keywords and forms a sentence used in conversation. The conversation manager 153 converts the text data of the sentence formed by the sentence formation unit 155 into voice signals through a voice converter 156 and outputs the voice data for the driver through a speaker 151.

FIG. 6 shows one example of the content of conversations for each stimulus level. As shown in FIG. 6, a conversation category "A" corresponding to the stimulus level "low" is used to draw a reflex response from the driver and requires little thinking by the driver. One example of such conversation is a typical conversation such as a greeting. A conversation category "B" corresponding to the stimulus level "medium" includes a short conversation formed based on the personal preference of the driver and is used to draw a simple response from the driver. This requires the driver to think. One example of such conversation includes, for example, the result of a soccer game when the favorite sport of the driver is soccer. A conversation category "C" corresponding to the stimulus level "high" includes a long conversation that continues connecting the scene where the vehicle 100 is traveling and the personal preference of the driver. This induces the driver to think and act. One example of such conversation, for example, when the destination of the vehicle 100 is set to Mt. Fuji, is a proposal of a recommended route taking into consideration the preference (e.g., food, shopping) of the driver including topics of Mt. Fuji and the weather.

As shown in FIG. 1, the alertness controller 130 also sends the information of the stimulus level selected referring to the stimulus level selection table T2 shown in FIG. 3 and the information of the stimulus strength corrected referring to the stimulus strength correction table T3 to a seat controller 160. If the stimulus level received from the alertness controller 130 is "medium" or "high" when receiving the information related to the stimulus level, the seat controller 160 executes the alertness control by vibrating the seat 161.

The alertness controller 130 also sends the information of the stimulus level selected referring to the stimulus level selection table T2 shown in FIG. 3 and the information of the stimulus strength corrected referring to the stimulus strength correction table T3 to an air conditioning controller 170. In the same manner, if the stimulus level received from the alertness controller 130 is "high" when receiving the information related to the stimulus level, the air conditioning controller 170 executes the alertness control by increasing or decreasing the blow amount of an air conditioner 171.

The alertness level determination unit 120 monitors changes in the driver alertness level after the alertness controller 130 performed the alertness control on the driver and determines the effectiveness of the alertness control. When the change amount of the driver alertness level is small and the effectiveness of the alertness control is not acknowledged, the alertness level determination unit 120 sends the determination result to the alertness controller 130. To effectively perform the alertness control on the driver, the alertness controller 130 increments the stimulus strength learned value P1 corresponding to a point of time when determined based on feedback information from the conversation controller 150, the seat controller 160, and the air conditioning controller 170. Subsequently, unless the effectiveness of the alertness control is acknowledged, the alertness controller 130 repeatedly performs the alertness control on the driver and increments the stimulus strength learned value P1. When the effectiveness of the alertness control is acknowledged, the sensitivity of the driver to the alertness stimulus is determined based on the corresponding stimulus strength learned value P1, and the personal alertness data D1 is updated based on the determination result. Consequently, in subsequent alertness control, even when a driver has a low sensitivity to the alertness stimulus, such characteristics of the driver is reflected. Thus, the alertness control may be effectively executed.

When executing the conversational alertness control, the conversation controller 150 analyzes the personal preference data of the driver based on the frequency of keywords appeared in the conversation or the like. The conversation controller 150 sends the analyzed personal preference data of the driver to the individual database 300 and updates the personal preference data D2. The conversation controller 150 may learn information related to the preference of the driver that is obtained through the conversation with the driver from a memory included in the vehicle 100.

The specific procedures of the alertness control executed by the vehicle alertness control system will now be described. When the ignition switch of the vehicle 100 is activated, the vehicle alertness control system repeatedly executes the alertness control shown in FIG. 7 in a predetermined cycle. For the sake of simplicity, FIG. 7 shows the process that is performed after the individual is specified.

The vehicle alertness control system uses the combination of the identification information of the electronic key 200 and the features of the voiceprint and the face of a driver to determine whether or not personal information of the driver has been specified by the individual specifying unit 114 (step S10A). When the personal information of the driver has not been specified (step S10A=NO), the personal information of the driver is specified by the individual specifying unit 114 (step S10B), and then the emotions of the driver are assumed by the emotion assumption unit 121 (step S11). When the personal information of the driver has been specified (step S10A=YES), the emotions of the driver are assumed by the emotion assumption unit 121 (step S11) without the process of step S10B. The emotions of the driver are assumed based on the voice expression feature amount of the driver received from the voice recognition unit 112, the face expression feature amount of the driver received from the image recognition unit 113, and the action feature amount of the driver received from the image recognition unit 113.

The vehicle alertness control system obtains biosignals of the driver through the biometric sensor 103 (step S12).

The vehicle alertness control system determines the driver alertness level using the alertness level determination unit 120 based on the driver emotion assumption result obtained by the emotion assumption unit 121 and the detection result of the biosignals of the driver obtained by the biometric sensor 103 (step S13).

The vehicle alertness control system detects the driving load on the driver using the driving load detector 140 (step S14).

Based on the driver alertness level determined in step S13 and the driving load on the driver detected in step S14, the vehicle alertness control system selects the stimulus level used in the alertness control using the alertness controller 130 and referring to the stimulus level selection table T2 (step S15).

To execute the alertness control that reflects the sensitivity of the driver to the alertness stimulus, the vehicle alertness control system uses the alertness controller 130 to obtain the personal alertness data D1 from the individual database 300 (step S16).

Based on the personal alertness data D1 obtained in step S16, the vehicle alertness control system corrects the stimulus strength corresponding to the stimulus level applied to the driver using the alertness controller 130 and referring to the stimulus strength correction table T3 through (step S17).

The vehicle alertness control system executes the alertness control under the condition of the stimulus strength that has been corrected in step S17 (step S18).

Figure 8:
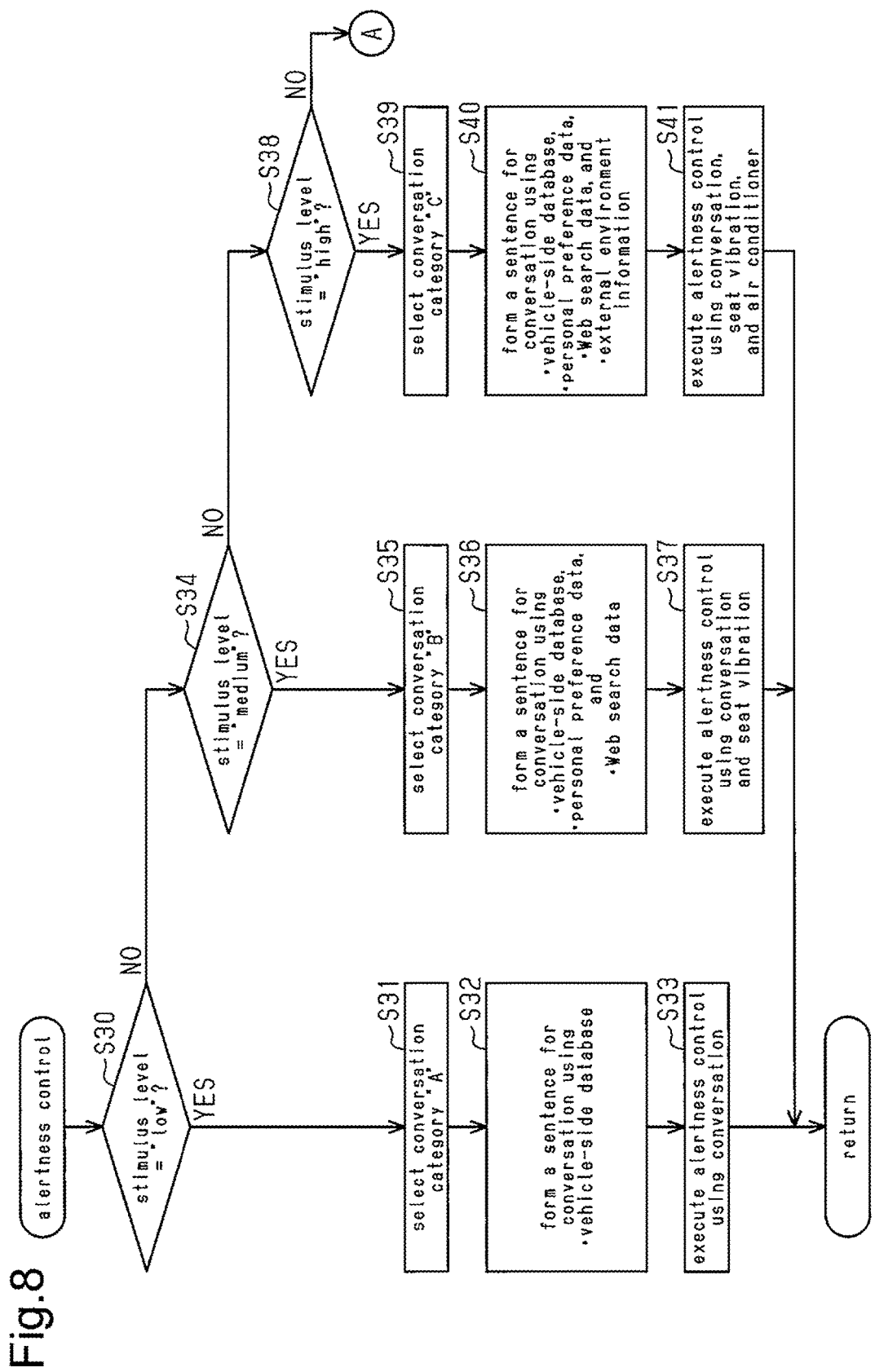
FIG. 8 is a flowchart showing the procedures for executing a subroutine of the alertness control shown in FIG. 7.

More specifically, as shown in FIG. 8, the vehicle alertness control system determines whether or not the stimulus level that has been determined in step S15 of FIG. 7 is "low" (step S30). When the stimulus level is "low" (step S30=YES), the vehicle alertness control system selects the conversation category "A," which is used to draw a reflex response from the driver and requires little thinking by the driver, using the conversation controller 150 (step S31). The vehicle alertness control system forms a sentence for conversation using the keyword W1, which is obtained from the vehicle-side database 154, in conformance with the conversation category "A" (step S32). Then, the vehicle alertness control system executes the conversational alertness control using the conversation controller 150 (step S33).

When the stimulus level determined in step S15 of FIG. 7 is not "low" (step S30=NO), the vehicle alertness control system determines whether or not the stimulus level is "medium" (step S34). When the stimulus level is "medium" (step S34=YES), the vehicle alertness control system selects the conversation category "B," which includes a short conversation formed based on the personal preference of the driver and is used to draw a simple response from the driver and requires the driver to think, using the conversation controller 150 (step S35). The vehicle alertness control system forms a sentence for conversation using the keywords W1, W2 obtained from the vehicle-side database 154, the personal preference data D2, and the Web search data D3A in conformance with the conversation category "B" (step S36). Then, the vehicle alertness control system executes the conversational alertness control using the conversation controller 150 (step S37). In this case, the vehicle alertness control system executes the seat vibration alertness control performed by the seat controller 160 together with the conversational alertness control performed by the conversation controller 150 (step S37).

When the stimulus level determined in step S15 of FIG. 7 is not "medium" (step S34=NO), the vehicle alertness control system determines whether or not the stimulus level is "high" (step S38). When the stimulus level is "high" (step S38=YES), the vehicle alertness control system selects the conversation category "C," which includes a long conversation that continues connecting the scene where the vehicle 100 is traveling and the personal preference of the driver and induces the driver to think and act, using the conversation controller 150 (step S39). The vehicle alertness control system forms a sentence for conversation using the keywords W1, W2 obtained from the vehicle-side database 154, the personal preference data D2, the Web search data D3A, and the external environment information in conformance with the conversation category "C" (step S40). Then, the vehicle alertness control system executes the conversational alertness control using the conversation controller 150 (step S41). In this case, the vehicle alertness control system executes the seat vibration alertness control performed by the seat controller 160 and the air conditioner alertness control performed by the air conditioning controller 170 together with the conversational alertness control performed by the conversation controller 150 (step S41).

When the stimulus level determined in step S15 of FIG. 7 is not "high" (step S38=NO), that is, when the stimulus level is "not set" or "control prohibited," the vehicle alertness control system does not execute the alertness control and returns to FIG. 7 to terminate the alertness control shown in FIG. 7.

Referring to FIG. 7, when the conversational alertness control is executed in step S18, the vehicle alertness control system analyzes the personal preference data of the driver based on the content of the conversation using the conversation controller 150 and updates the personal preference data D2 (step S19).

The vehicle alertness control system monitors changes in the driver alertness level after the alertness control is executed using the alertness level determination unit 120 to determine the effectiveness of the alertness control (step S20). When the effectiveness of the alertness control is not acknowledged (step S20=NO), the vehicle alertness control system increments the stimulus strength learned value P1 using the alertness controller 130 to effectively perform the alertness control on the driver. Then, the vehicle alertness control system upwardly corrects the stimulus strength applied to the driver referring to the stimulus strength correction table T3 (step S21). The vehicle alertness control system returns to step S18 and again executes the alertness control of step S18 under the condition of the upwardly corrected stimulus strength. Subsequently, unless the stimulus strength learned value P1 reaches an upper limit value (refer to FIG. 4), the vehicle alertness control system repeatedly increments the stimulus strength learned value P1 and updates the personal preference of the driver based on the conversational alertness control until the effectiveness of the alertness control is acknowledged.

When the effectiveness of the alertness control is acknowledged (step S20=YES), the vehicle alertness control system determines the sensitivity of the driver to the alertness stimulus based on the corresponding stimulus strength learned value P1 using the conversation controller 150 and updates the personal alertness data D1 based on the determination result (step S22). Then, the vehicle alertness control system terminates the alertness control shown in FIG. 7.

The operation of the vehicle alertness control system of the present embodiment will now be described.

Referring to section (a) of FIG. 9, for example, when the vehicle is traveling and the driver alertness level is decreased, it is desirable that alertness control be executed to increase the driver alertness level. However, the alertness control may increase a burden of the driver depending on the amount of the driving load on the driver when the vehicle is traveling. Such a shortcoming tends to be significant particularly in alertness control that involves the driver as a partner such as the conversational alertness control.

In this regard, as shown in section (b) of FIG. 9, the present embodiment monitors the driving load on the driver in addition to the driver alertness level when the vehicle is traveling. As shown in section (c) of FIG. 9, the alertness control is not executed when the driving load on the driver is determined to be high. This prevents a situation in which the alertness control increases a burden of the driver. When the driving load on the driver becomes low, the alertness control is executed. This effectively increases the alertness degree of the driver.

Normally, as the driver alertness level is decreased, the level of a stimulus needed to increase the alertness level becomes higher. Thus, in the present embodiment, as shown in section (c) of FIG. 9, the stimulus level applied to the driver is increased as the driver alertness level is decreased.

More specifically, as shown in section (d) of FIG. 9, as the driver alertness level is decreased, the conversational alertness control increases the frequency of topics that easily attract the interest of the driver, for example, a topic reflecting the preference of the driver or a topic of the present external environment information of the vehicle 100. Thus, even when the driver alertness level is decreased and strong alertness control is needed to improve the alertness level, such a situation can be appropriately coped with.

Additionally, as shown in sections (e) and (f) of FIG. 9, when the driver alertness level is low, the conversational alertness control is combined with the alertness control by vibrating the seat 161 and the alertness control by adjusting the air conditioner 171. This further increases the effectiveness.

The ID verification unit 111, the voice recognition unit 112, the image recognition unit 113, the individual specifying unit 114, the alertness level determination unit 120 including the emotion assumption unit 121, the alertness controller 130, the driving load detector 140, the conversation controller 150, the seat controller 160, and the air conditioning controller 170, which are included in the vehicle alertness control system, may be implemented by one or more processors (control circuitry) that operate in accordance with one or more dedicated hardware circuit and/or a computer program (software). The processor includes a CPU and memories such as a RAM and a ROM. The memories store program codes or commands configured for the processor to execute, for example, the processes shown in FIGS. 7 and 8. The memories, or computer readable media, include any applicable medium that can be accessed by a versatile or dedicated computer.

Accordingly, the present embodiment has the advantages described below.

(1) The alertness controller 130 determines the stimulus level applied to the driver based on the determination result of the driver alertness level obtained by the alertness level determination unit 120. The conversation controller 150 selects the conversation category that corresponds to the determined stimulus level. This changes the degree of involving the driver in the conversation in accordance with the driver alertness level and effectively increases the driver alertness level.

(2) When the driver needs to concentrate on the driving operation, for example, when traveling on a curve, conversation of the alertness control may adversely increase a burden of the driver. Under such a situation, the alertness controller 130 prohibits execution of the alertness control including the conversation. This limits the burden that the alertness control applies to the driver.

(3) The conversation controller 150 is configured to be able to access the personal preference data D2, which is information related to the personal preference of the driver. The conversation controller 150 executes control that increases the frequency of the information related to the preference of the driver appeared in the conversation as the alertness controller 130 selects a higher stimulus level. Thus, as the driver alertness level decreases and the stimulus level corresponding to the driver alertness level increases, more topics that easily attract the interest of the driver are provided in conformance with the preference of the driver. This achieves the conversational alertness control that further improves the awakening effect.

(4) The conversation controller 150 includes the information related to the preference of the driver in the conversation only when the driver alertness level determined by the alertness level determination unit 120 is "D3" or "D4," which is relatively low. Thus, the frequency of the information related to the preference of the driver appeared in the conversation may be easily controlled for each driver alertness level.

(5) The personal preference data D2, which indicates the personal preference of the driver, includes data obtained during the conversation with the driver in the conversational alertness control. Thus, the information of the personal preference data D2, which is related to the preference of the driver, is updated whenever the conversational alertness control is executed. This obtains highly reliable alertness control that further reflects the preference of the driver as the vehicle alertness control system is used more frequently.

(6) The conversation controller 150 is configured to be able to access the in-vehicle information terminal 180, which collects the external environmental information including the location information of the vehicle 100. The conversation controller 150 executes control that increases the frequency of the topic related to the present external environmental information of the vehicle 100 appeared in the conversation as the alertness controller 130 selects a higher stimulus level. Thus, as the driver alertness level decreases and the stimulus level corresponding to the driver alertness level increases, more topics of the present external environmental information of the vehicle 100, which interest the driver, are provided. This achieves the conversational alertness control that further improves the awakening effect.

(7) When the alertness controller 130 performs the alertness control on the driver, the alertness level determination unit 120 monitors changes in the driver alertness level after the stimulus is applied and determines the effectiveness of the alertness control. When determined that the effectiveness of the alertness control is not acknowledged, the stimulus strength learned value P1 is incremented. This increases the strength of the alertness stimulus applied to the driver. Thus, even when a driver has a low sensitivity to the alertness control, such characteristics of the driver may be reflected and the alertness control may be effectively executed.

(8) When the driver alertness level is low, the conversational alertness control performed by the conversation controller 150 is combined with the vibration alertness control performed by the seat controller 160 on the seat 161 and the air conditioner alertness control performed by the air conditioning controller 170 on the air conditioner 171. This achieves the alertness control that further improves the awakening effect.

It should be apparent to those skilled in the art that the present invention may be embodied in many other specific forms without departing from the scope of the invention. Particularly, it should be understood that the present invention may be embodied in the following forms.

In the embodiment, the present external environment information of the vehicle 100 is collected from the in-vehicle information terminal 180. Instead, the external environment information may be collected from the car navigation system 109.

In the embodiment, whenever the stimulus strength learned value P1 is incremented, each parameter (conversation period P2, seat vibration strength P3, seat vibration cycle P4, and air conditioner blow amount P5) that sets the strength of the alertness stimulus is changed by a fixed value. Instead, whenever the stimulus strength learned value P1 is incremented, for example, the change amount of each parameter may be increased, decreased, or the like in accordance with the stimulus strength learned value P1. In the embodiment, the parameters are changed in the same condition in accordance with the driver alertness level without depending on the stimulus level selected in correspondence with the driver alertness level. Instead, the condition that changes the parameters may be set for each stimulus level in different manners.

In the embodiment, the conversational alertness control is combined with the alertness control by vibrating the seat 161 and the alertness control by adjusting the air conditioner 171. Instead, without the combination with the vibration of the seat 161 and the adjustment of the air conditioner 171, the strength of the alertness stimulus may be changed only by changing the conversation category.

For the sake of convenience, particularly, in the conversational control, the embodiment includes a first alertness level that corresponds to, for example, the level "D2" and a second alertness level that has a smaller alertness degree than the first alertness level and corresponds to, for example, the levels "D3" and "D4." Additionally, as the stimulus levels corresponding to the alertness levels, the embodiment includes a first stimulus level that is selected based on the first alertness level and corresponds to the "low" level and a second stimulus level that is selected based on the second alertness level and corresponds to the "medium" and "high" levels. The second stimulus level has a stronger stimulus than the first stimulus level. The conversation controller 150 selects a conversation category that does not include information related to the preference of the driver registered in the database (personal preference data D2) as the conversation category corresponding to the first stimulus level. The conversation controller 150 selects a conversation category that includes information related to the preference of the driver registered in the database as the conversation category corresponding to the second stimulus level. However, such control is just one example of control that the conversation controller 150 executes. For example, as the conversation category corresponding to the second stimulus level, the conversation controller 150 may increase the ratio (number) of a keyword related to the preference relative to other keywords in the conversation, shorten the cycle in which the keyword related to the preference appears, or increase the variety of keywords related to the preference compared to the conversation category corresponding to the first stimulus level. More specifically, the conversation controller 150 only needs to be configured to be able to access the database in which the information related to the preference of the driver is registered and execute control that increases the frequency of the information related to the preference of the driver that is read from the database and appears in the conversation as the alertness controller 130 selects a higher stimulus level. Additionally, the conversation controller 150 only needs to be configured to be able to access the in-vehicle information terminal 180, which collects the external environment information including the location information of the vehicle 100, and execute control that increases the frequency of the information that is related to the present external environment of the vehicle 100 and collected from the in-vehicle information terminal 180 as the alertness controller 130 selects a higher stimulus level.

In the embodiment, the driver alertness level is determined based on both the emotion assumption result obtained from the behavior of the driver and the detection result of the biosignals of the driver. However, the driver alertness level may be determined based on only one of them.

The present examples and embodiments are to be considered as illustrative and not restrictive, and the invention is not to be limited to the details given herein, but may be modified within the scope and equivalence of the appended claims.

The invention claimed is:

1. A vehicle alertness control system configured to execute alertness control that increases an alertness of a driver of a vehicle, the vehicle alertness control system comprising:
   an alertness level determination unit configured to determine an alertness level, which is a hierarchized degree of the alertness of the driver, based on at least one of an assumption result obtained from an emotion assumption unit that is configured to monitor behavior of the driver and assume an emotion of the driver and a detection result obtained from a biometric sensor that detects a biosignal of the driver;
   an alertness controller configured to select a level of a stimulus applied to the driver based on the determined alertness level; and
   a conversation controller configured to select a conversation category corresponding to the selected stimulus level and control conversation with the driver through a speaker and a microphone, wherein the conversation category is selected from conversation categories categorizing a content of utterance in correspondence with each stimulus level.

2. The vehicle alertness control system according to claim 1, further comprising:
   a driving load detector configured to detect a driving load on the driver based on a traveling state of the vehicle,
   wherein when a driving load detection value obtained by the driving load detector is greater than or equal to a predetermined value, the alertness controller is configured to prohibit execution of alertness control, in which the conversation is performed, by the conversation controller.

3. The vehicle alertness control system according to claim 1, wherein the conversation controller is configured to be able to access a database in which information related to a preference of the driver is registered and increase a frequency the information related to the preference, which is read from the database, appears in the conversation as the alertness controller selects a higher stimulus level.

4. The vehicle alertness control system according to claim 3, wherein
   the alertness level includes a first alertness level and a second alertness level that has a lower alertness degree than the first alertness level,
   the stimulus level includes a first stimulus level that is selected based on the first alertness level and a second stimulus level that is selected based on the second alertness level and has a stronger stimulus than the first alertness level,
   the conversation category includes a first conversation category, which does not include the information related to the preference and is registered in the database, and a second conversation category, which includes the information related to the preference and is registered in the database, and
   the conversation controller is configured to select the first conversation category as a conversation category corresponding to the first stimulus level and the second conversation category as a conversation category corresponding to the second stimulus level.

5. The vehicle alertness control system according to claim 3, wherein the database, in which the information related to the preference of the driver is registered, includes information related to a preference that is obtained during conversation with the driver.

6. The vehicle alertness control system according to claim 1, wherein the conversation controller is configured to be able to access an in-vehicle information terminal that collects external environment information including location information of the vehicle, and the conversation controller is configured to increase a frequency information related to a present vehicle external environment collected by the in-vehicle information terminal appears in the conversation as the alertness controller selects a higher stimulus level.

7. A vehicle alertness control system configured to execute alertness control that increases an alertness of a driver of a vehicle, the vehicle alertness control system comprising:
   a control circuitry, wherein the control circuitry is configured to
   execute at least one of monitoring behavior of the driver to assume an emotion of the driver and receiving a detection result from a biometric sensor that detects a biosignal of the driver,
   determine an alertness level, which is a hierarchized degree of the alertness of the driver, based on at least one of the driver emotion assumption result and the detection result of the biometric sensor,
   select a level of a stimulus applied to the driver based on the determined alertness level,
   select a conversation category that corresponds to the selected stimulus level from conversation categories that categorize a content of utterance corresponding to each stimulus level, and
   control conversation with the driver through a speaker and a microphone.

8. A method executed by a control system, the method comprising:
   at least one of monitoring behavior of a driver of a vehicle to assume an emotion of the driver and receiving a detection result from a biometric sensor that detects a biosignal of the driver;
   determining an alertness level, which is a hierarchized alertness degree of the driver,
   based on at least one of the driver emotion assumption result and the detection result of the biometric sensor;
   selecting a level of a stimulus applied to the driver based on the determined alertness level;
   selecting a conversation category corresponding to the selected stimulus level from conversation categories that categorize a content of utterance in correspondence with each stimulus level; and
   controlling conversation with the driver through a speaker and a microphone.

* * * * *